United States Patent
Pollak

(10) Patent No.: US 10,779,936 B2
(45) Date of Patent: Sep. 22, 2020

(54) PERCUTANEOUSLY-DEPLOYABLE PROSTHETIC TRICUSPID VALVE

(71) Applicant: Mayo Foundation for Medical Education and Research, Rochester, MN (US)

(72) Inventor: Peter M. Pollak, Atlantic Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 190 days.

(21) Appl. No.: 15/574,683

(22) PCT Filed: May 11, 2016

(86) PCT No.: PCT/US2016/031730
§ 371 (c)(1),
(2) Date: Nov. 16, 2017

(87) PCT Pub. No.: WO2016/186909
PCT Pub. Date: Nov. 24, 2016

(65) Prior Publication Data
US 2018/0289472 A1 Oct. 11, 2018

Related U.S. Application Data

(60) Provisional application No. 62/163,102, filed on May 18, 2015.

(51) Int. Cl.
*A61F 2/24* (2006.01)

(52) U.S. Cl.
CPC .......... *A61F 2/2418* (2013.01); *A61F 2/2412* (2013.01); *A61F 2/2439* (2013.01); *A61F 2210/0014* (2013.01); *A61F 2230/0067* (2013.01)

(58) Field of Classification Search
CPC .... A61F 2/2412; A61F 2/2418; A61F 2/2439; A61F 2/2427; A61F 2/2436; A61F 2/2409; A61F 2/2466; A61F 2210/0014; A61F 2230/0067
See application file for complete search history.

(56) References Cited

U.S. PATENT DOCUMENTS

| | | | |
|---|---|---|---|
| 2006/0020327 A1* | 1/2006 | Lashinski | A61F 2/2436 623/1.25 |
| 2006/0052867 A1* | 3/2006 | Revuelta | A61F 2/2418 623/2.18 |
| 2006/0259135 A1* | 11/2006 | Navia | A61F 2/2409 623/2.11 |

(Continued)

OTHER PUBLICATIONS

PCT International Search Report and Written Opinion in International Appln. No. PCT/US2016/31730, dated Aug. 11, 2016, 12 pages.

(Continued)

*Primary Examiner* — Jocelin C Tanner
(74) *Attorney, Agent, or Firm* — Fish & Richardson P.C.

(57) ABSTRACT

Devices and methods for the treatment of heart conditions are provided herein. For example, this document provides devices and methods for treating tricuspid valve regurgitation by percutaneously implanting a prosthetic tricuspid valve.

19 Claims, 3 Drawing Sheets

(56) References Cited

U.S. PATENT DOCUMENTS

| | | | |
|---|---|---|---|
| 2007/0005131 A1* | 1/2007 | Taylor | A61F 2/2433 623/2.11 |
| 2011/0276128 A1* | 11/2011 | Cao | A61F 2/2409 623/2.11 |
| 2012/0053681 A1* | 3/2012 | Alkhatib | A61F 2/2409 623/2.11 |
| 2013/0172978 A1* | 7/2013 | Vidlund | A61B 17/0401 623/1.12 |
| 2014/0277410 A1* | 9/2014 | Bortlein | A61F 2/2427 623/2.11 |
| 2014/0303179 A1 | 10/2014 | Cox et al. | |
| 2014/0303719 A1* | 10/2014 | Cox | A61F 2/2418 623/2.11 |

OTHER PUBLICATIONS

PCT International Preliminary Report on Patentability in International Appln. No. PCT/US2016/31730, dated Nov. 21, 2017, 7 pages.

* cited by examiner

PERCUTANEOUSLY-DEPLOYABLE PROSTHETIC TRICUSPID VALVE

CROSS-REFERENCE TO RELATED APPLICATIONS

This application claims the benefit of U.S. Provisional Application Ser. No. 62/163,102, filed May 18, 2015. The disclosure of the prior application is considered part of (and is incorporated by reference in) the disclosure of this application.

BACKGROUND

1. Technical Field

This document relates to devices and methods for the treatment of heart conditions. For example, this document relates to devices and methods for treating tricuspid valve regurgitation by percutaneously implanting a prosthetic tricuspid valve.

2. Background Information

Tricuspid regurgitation is a common problem presenting unique challenges. Patients with significant tricuspid regurgitation have chronic difficulty with fluid retention and low cardiac output.

The right ventricle and tricuspid annulus is comparatively thinner and less substantial than the left ventricle and mitral annulus. Additionally, the right ventricle and tricuspid annulus are subject to change in shape and dimensions with fluctuations in volume status and pulmonary pressure. There is also less tissue available to hold a device in place, and outward radial forces may distort the anatomy. The tricuspid valve also tends to have a somewhat ovaloid annulus.

SUMMARY

This document provides devices and methods for the treatment of heart conditions. For example, this document provides devices and methods for treating tricuspid valve regurgitation by percutaneously implanting a prosthetic tricuspid valve.

In one implementation, a prosthetic tricuspid valve includes a structural framework comprising one or more braided nitinol wires, a cuff disposed on a proximal end portion of the outer surface, a plurality of anchor features, and a valve assembly disposed within the inner open region. The valve assembly includes three leaflets that are configured for coaptation with each other. The structural framework is arranged to define an outer surface and an inner open region. The cuff comprises a flexible covering material. The anchor features extend outward from the outer surface. The anchor features are configured for piercing tissue. The prosthetic tricuspid valve is reconfigurable between a low-profile delivery configuration for containment within a delivery catheter and an expanded deployed configuration.

Such a prosthetic tricuspid valve may optionally include one or more of the following features. The structural framework may comprise a frustoconical shape. The flexible covering material may comprise ePTFE or PTFE. At least some of the anchor features may extend outward from the outer surface at angles in a range from about 50° to about 90°. At least some of the anchor features may extend outward from the outer surface for distances in a range of about 0.6 mm to about 1.0 mm.

In another implementation, a prosthetic tricuspid valve deployment system includes a delivery catheter that defines a lumen therein, a prosthetic tricuspid valve, and a control string. The control string is slidably engaged with the structural framework such that tensioning the control string can cause the structural framework to contract, and slackening the control string can allow the structural framework to expand. The prosthetic tricuspid valve is reconfigurable between a low-profile delivery configuration for containment within the lumen and an expanded deployed configuration. The delivery catheter is configured for percutaneous use. The prosthetic tricuspid valve includes a structural framework comprising one or more braided nitinol wires, a cuff disposed on a proximal end portion of the outer surface, a plurality of anchor features, and a valve assembly disposed within the inner open region. The valve assembly comprises three leaflets that are configured for coaptation with each other. The anchor features extend outward from the outer surface. The anchor features are configured for piercing tissue the structural framework arranged to define an outer surface and an inner open region. The cuff comprises a flexible covering material.

Such a prosthetic tricuspid valve deployment system may optionally include one or more of the following features. A distal end portion of the delivery catheter may be selectively deflectable. The structural framework may comprise a frustoconical shape. The flexible covering material may comprise ePTFE or PTFE. At least some of the anchor features may extend outward from the outer surface at angles in a range from about 50° to about 90°. At least some of the anchor features may extend outward from the outer surface for distances in a range of about 0.6 mm to about 1.0 mm.

In another implementation, a method of implanting a prosthetic tricuspid valve in a patient includes percutaneously installing a delivery catheter in the patient, navigating the delivery catheter within the patient such that a distal end of the delivery catheter is position adjacent a native tricuspid valve of the patient, and causing the prosthetic tricuspid valve to emerge from the lumen and to expand within the native tricuspid valve. The delivery catheter defines a lumen therein. The prosthetic tricuspid valve is disposed within the lumen in a low-profile delivery configuration. In some embodiments, the prosthetic tricuspid valve includes (a) a structural framework comprising one or more braided nitinol wires, the structural framework arranged to define an outer surface and an inner open region; (b) a cuff disposed on a proximal end portion of the outer surface, the cuff comprising a flexible covering material; (c) a plurality of anchor features, the anchor features extending outward from the outer surface, the anchor features configured for piercing tissue; and (d) a valve assembly disposed within the inner open region. The valve assembly comprises three leaflets that are configured for coaptation with each other. A majority of the prosthetic tricuspid valve is disposed below an annulus of the native tricuspid valve and within a right ventricle of the patient.

Such a method of implanting a prosthetic tricuspid valve in a patient may optionally include one or more of the following features. The causing the prosthetic tricuspid valve to emerge from the lumen and to expand within the native tricuspid valve may also cause at least some of the anchor features to penetrate one or more native leaflets of the native tricuspid valve. The method may further comprise a control string. The control string may be slidably engaged with the structural framework such that tensioning the control string can cause the structural framework to contract and slackening the control string can allow the structural framework to expand. The method may further comprise, after causing the prosthetic tricuspid valve to emerge from the lumen and to expand within the native tricuspid valve, tensioning the control string to contract the structural framework such that the at least some of the anchor features that penetrated the one or more native leaflets are no longer penetrating the one or more native leaflets, and repositioning the prosthetic tricuspid valve within the native tricuspid valve.

Particular embodiments of the subject matter described in this document can be implemented to realize one or more of the following advantages. In some embodiments, heart conditions such as tricuspid valve regurgitation and others can be treated using the devices and methods provided herein. In some embodiments, various heart conditions such as tricuspid valve regurgitation can be treated in a minimally invasive fashion using the devices and methods provided herein. Such minimally invasive techniques can reduce recovery times, patient discomfort, and treatment costs. In some embodiments, the prosthetic tricuspid valves provided herein exert a low level of radial force to the native anatomy, thereby advantageously minimizing the inducement of distortions to the native anatomy. In some embodiments, integral anchor features are included in the prosthetic tricuspid valves provided herein and such anchor features provide migration resistance in relation to the native tricuspid valve. In particular embodiments, one or more cuffs are included on the prosthetic tricuspid valve. Such cuffs can enhance the performance of the prosthetic tricuspid valve to mitigate leaks and/or regurgitation. Other advantages will be apparent from the descriptions provided below.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

Figure 1:
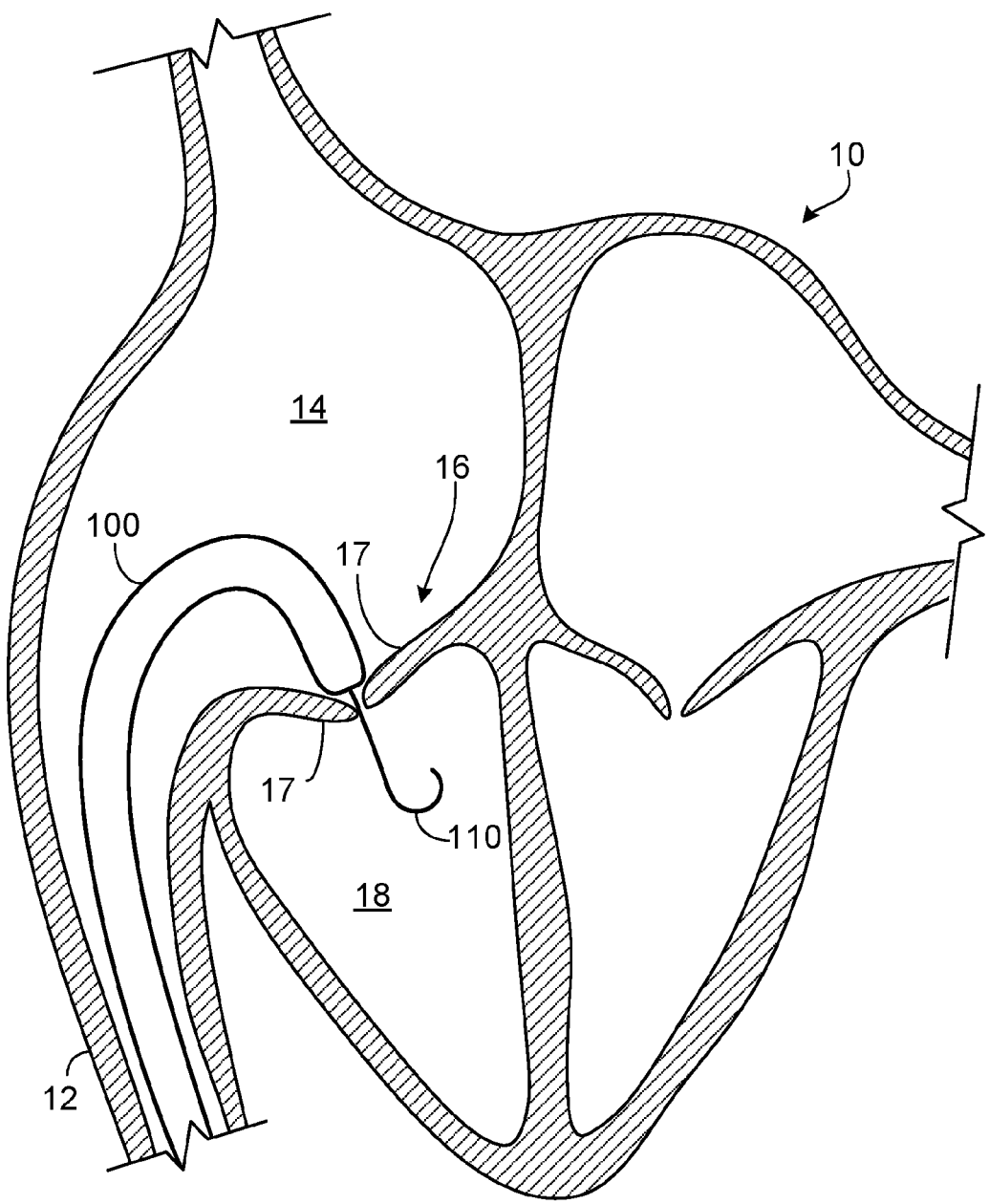
FIG. 1 is a schematic diagram of human patient's heart undergoing a procedure to implant a prosthetic tricuspid valve using a catheter-based delivery system in accordance with some embodiments provided herein.

This document provides devices and methods for the treatment of heart conditions. For example, this document provides devices and methods for treating tricuspid valve regurgitation by percutaneously implanting a prosthetic tricuspid valve.

Some embodiments of the prosthetic tricuspid valve devices provided herein are composed of a nitinol mesh structural framework that supports an integral tri-leaflet valve. The prosthetic tricuspid valves are reconfigurable between a low-profile delivery configuration and an expanded deployed configuration. As such, the prosthetic tricuspid valves provided herein are deliverable and deployable through a patient's vasculature using a transcatheter technique. For example, in some implementations the prosthetic tricuspid valve is initially contained within a delivery catheter that can be percutaneously introduced into the patient through a transvenous puncture. Using imaging (e.g., fluoroscopy) a clinician can navigate the delivery catheter (or sheath) containing the prosthetic tricuspid valve to a target site within the patient. In some embodiments, the delivery catheter is deflectable/steerable.

At the target site (for example, at the native tricuspid valve site), the prosthetic tricuspid valve can be made to emerge from the delivery catheter so that the valve expands to its deployed configuration within the native tricuspid valve anatomy. Upon emergence from the delivery catheter, the prosthetic tricuspid valve expands to conform with the native anatomy. In some embodiments, the prosthetic tricuspid valve self-expands. In some embodiments, a balloon catheter is used to cause the prosthetic tricuspid valve to expand. In some embodiments, a combination of self-expansion and assisted expansion is used.

In some embodiments, the prosthetic tricuspid valve includes small anchor features (e.g., barbs, spikes, hooks, penetrating members, and the like). The anchor features can penetrate into the native tissue at the implant site. For example, in some implementations the anchor features penetrate into the native tricuspid valve leaflets. The anchor features provide migration resistance for the prosthetic tricuspid valves.

Because the right ventricle (RV) is relatively thin and changes dimension with changes in volume and pressure loading, in some embodiments the prosthetic tricuspid valves provided herein are designed to exert a low or minimal level of radial force to the native anatomy. In some embodiments, the radial forces from the nitinol stent framework become progressively lower toward the distal edge of the prosthetic tricuspid valve. This allows the prosthetic tricuspid valve substantial conformability so that the prosthetic tricuspid valve can adapt of to the size and shape of the RV and native tricuspid valve annulus. With less tricuspid regurgitation as a result of the use of the prosthetic tricuspid valves provided herein, the dimension of the RV tends to decrease, along with the size of the tricuspid annulus. The prosthetic tricuspid valves provided herein are designed to accommodate that change while remaining fully functional.

In some embodiments, one or more cuffs of material are included on the prosthetic tricuspid valve. Such a cuff is provided, for example, to limit perivalvular and per-valvular regurgitation. In some embodiments, a surrounding string (e.g., lasso, purse string, and the like) can be included to assist with deployment, retrieval, and repositioning of the prosthetic tricuspid valve.

In some embodiments, the prosthetic tricuspid valves provided herein are meant to be implanted in a position that is biased towards the ventricular side of the tricuspid annulus. As such, the prosthetic tricuspid valve can substantially avoid interaction with the coronary sinus or conduction tissue of the right atrium.

Referring to FIG. 1, a human patient's heart 10 with a native tricuspid valve 16 can receive a prosthetic tricuspid valve delivery catheter 100. Heart 10 includes the native tricuspid valve leaflets 17 and the right ventricle 18.

In one non-limiting example implementation, prosthetic tricuspid valve delivery catheter 100 can be navigated through the patient's vasculature, such as through the inferior vena cava 12 and into the right atrium 14. However, other approaches to the native tricuspid valve 16 are also contemplated and within the scope of this disclosure. A guidewire 110 and imagining techniques (e.g., fluoroscopy, echocardiography, and the like) can be used to assist with the inter-vascular navigation and placement of delivery catheter 100. One or more radiopaque markers may be included on delivery catheter 100 (and on the prosthetic tricuspid valve) to provide enhanced fluoroscopic visibility.

In some embodiments, delivery catheter 100 is steerable. That is, in some embodiments at least the distal tip portion of delivery catheter 100 is selectively deflectable as desired by a clinician (e.g., interventional cardiologist). As such, in some embodiments delivery catheter 100 can advantageously make tight bends as depicted in FIG. 1. The prosthetic tricuspid valve can be preloaded in the distal end portion of delivery catheter 100 while in the low-profile delivery configuration.

While in the depicted embodiment, the delivery system for the prosthetic tricuspid valve is illustrated as comprising delivery catheter 100 and guidewire 110, it should be understood that other components may be included as part of the delivery system. For example, other catheters, balloon devices, control devices, and the like, can be included in some embodiments of the delivery system used to deploy the prosthetic tricuspid valve devices provided herein.

Figure 2:
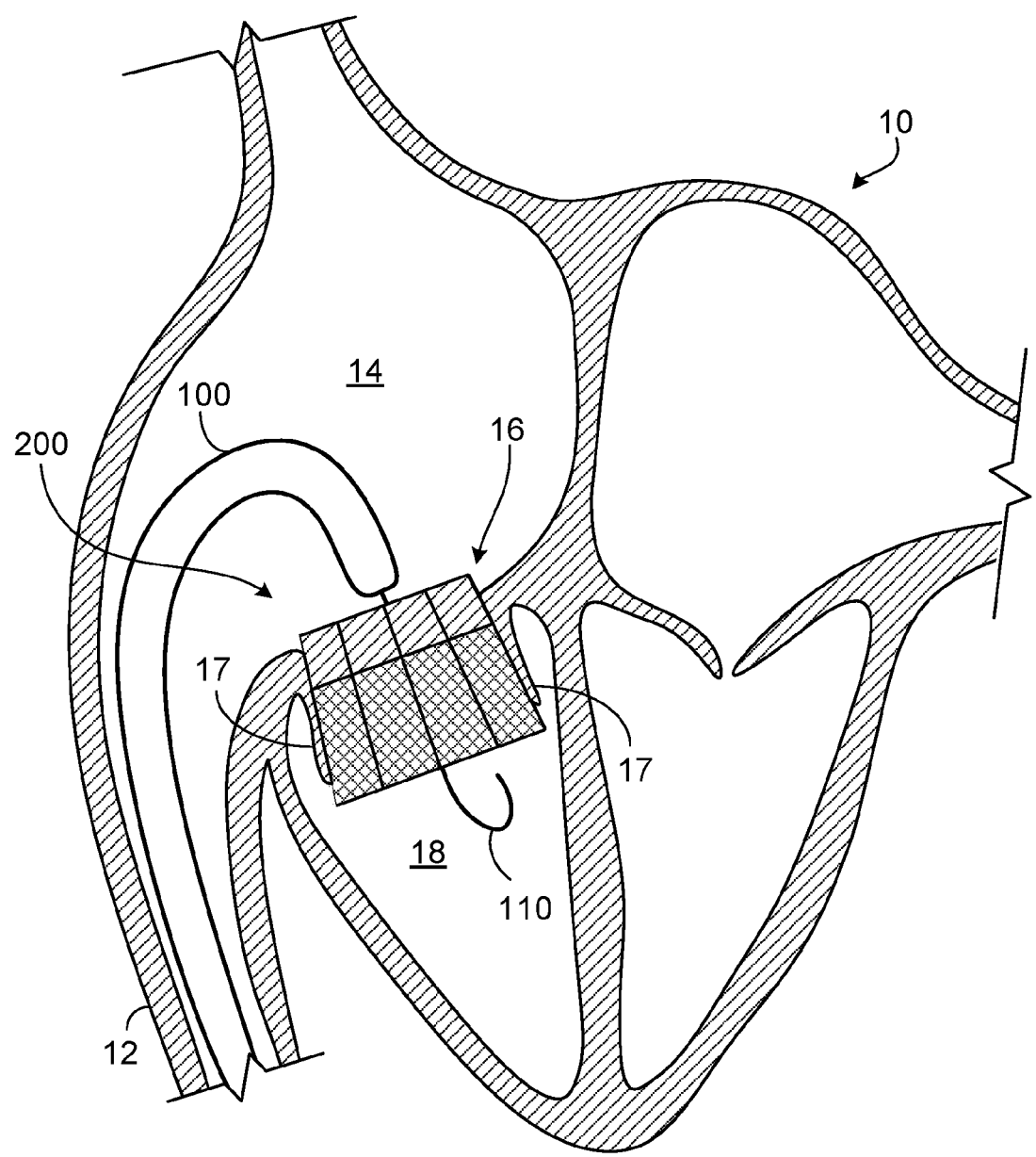
FIG. 2 is the schematic diagram of FIG. 1 with the prosthetic tricuspid valve implanted within the patient's native tricuspid valve in accordance with some embodiments provided herein.

Referring to FIG. 2, a prosthetic tricuspid valve 200 can been implanted in engagement with native tricuspid valve 16 by causing prosthetic tricuspid valve 200 to emerge from delivery catheter 100. Upon emergence from delivery catheter 100, prosthetic tricuspid valve 200 can expand to conform to native tricuspid valve 16. In some embodiments, prosthetic tricuspid valve 200 self-expands. In some embodiments, a balloon catheter is used to cause prosthetic tricuspid valve 200 to expand. In some embodiments, a combination of self-expansion and assisted expansion is used.

In some implementations, prosthetic tricuspid valve 200 is implanted such that native tricuspid valve leaflets 17 are in contact with the outer surface of prosthetic tricuspid valve 200. In some embodiments, as described further below, anchor features on the outer surface of prosthetic tricuspid valve 200 penetrate into surrounding native tissue, such as native tricuspid valve leaflets 17, to provide migration resistance (while allowing for repositioning and retrievability). As depicted, in some implementations prosthetic tricuspid valve 200 is implanted in a position that is biased towards right ventricle 18.

In some embodiments, prosthetic tricuspid valve 200 exerts a low level of radial force to the native anatomy, such as the annulus of native tricuspid valve 16. In some embodiments, the radial forces from the nitinol stent framework of prosthetic tricuspid valve 200 become progressively lower toward the distal edge (in the direction from right atrium 14 towards right ventricle 18) of prosthetic tricuspid valve 200. This allows prosthetic tricuspid valve 200 substantial conformability so that prosthetic tricuspid valve 200 can adapt of to the size and shape of RV 18 and the annulus of native tricuspid valve 16 without inducing substantial deformation to the size and shape of the native anatomy.

Figure 4:
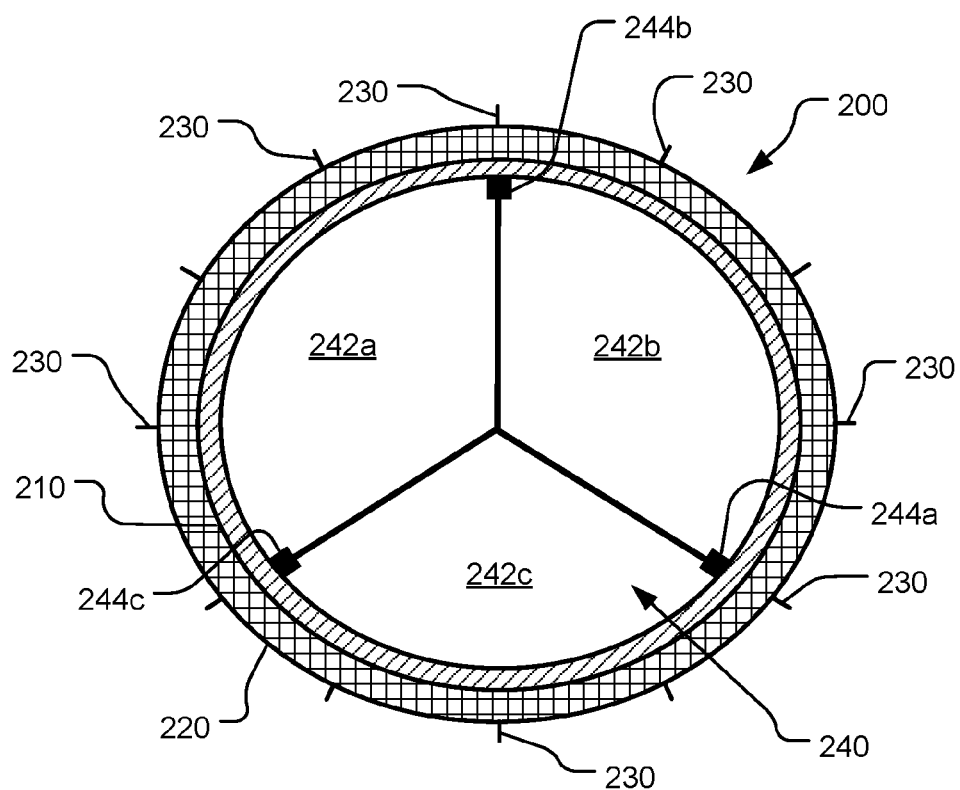
FIG. 4 is a top view of the prosthetic tricuspid valve of FIG. 3.
Figure 3:
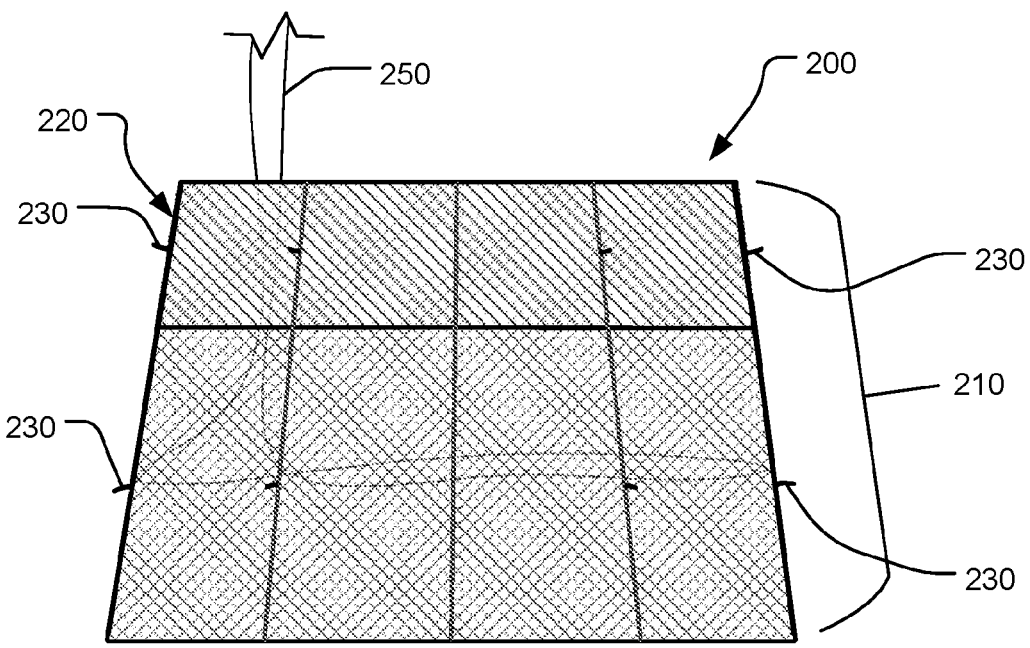
FIG. 3 is a side view of a prosthetic tricuspid valve in accordance with some embodiments provided herein.

Referring to FIGS. 3 and 4, in some embodiments provided herein, prosthetic tricuspid valve 200 includes a structural framework 210 that supports an integral tri-leaflet valve assembly 240.

In some embodiments, structural framework 210 is comprised of a metallic material such as nitinol, stainless steel, or combinations thereof. In some embodiments, structural framework 210 is a mesh material. For example, in some embodiments structural framework 210 is partially or entirely comprised of a braided or wound material such as strands of nitinol wire. In some embodiments, structural framework 210 is partially or entirely comprised of a material that is cut and expanded, such as a tube or sheet of nitinol material.

In some embodiments, such as the depicted embodiment, structural framework 210 defines (in its naturally shape, which may be a heat-set shape) a slightly ovular or oblong cross-sectional shape (i.e., non-circular). Such a shape may facilitate a general inherent conformance in correspondence with the shape of a native tricuspid valve. In some embodiments, other cross-sectional shapes may be defined by structural framework 210 (e.g., circular), and in some embodiments the cross-sectional shape can vary along the longitudinal length of structural framework 210. Such variations may enhance the conformance between prosthetic tricuspid valve 200 and the native anatomy to thereby facilitate good migration resistance while exerting minimal radial forces.

As seen in FIG. 3, in some embodiments structural framework 210 flares outward in the distal direction. That is, in some embodiments structural framework 210 is generally frustoconical in shape. However, in some embodiments structural framework 210 defines a difference shape (e.g., generally cylindrical). While in the depicted embodiment structural framework 210 defines a generally linear outer wall profile, in some embodiments some or all wall portions are curved or contoured. Structural framework 210 defines an inner open region.

In some embodiments, some or all of structural framework 210 is covered with a covering material. Such a covering may enhance sealing between prosthetic tricuspid valve 200 and the native anatomy, and may also enhance migration resistance in some circumstances. The covering may be a natural or a synthetic material. In some embodiments, the covering material, or portions thereof, comprise a fluoropolymer, such as polytetrafluoroethylene (PTFE) or an expanded polytetrafluoroethylene (ePTFE) polymer. In some embodiments, the covering material, or portions thereof, comprises a polyester, a silicone, a urethane, other biocompatible polymers, DACRON®, copolymers, or combinations and subcombinations thereof. In some embodiments, the covering material can include natural tissues such as, but not limited to, bovine, porcine, ovine, or equine pericardium. In some such embodiments, the tissues are chemically treated using glutaraldehyde or formaldehyde or triglycidylamine (TGA) solutions or other tissue crosslinking agents.

In some embodiments, the covering material can be modified by one or more chemical or physical processes that enhance certain physical properties of the covering material. For example, a hydrophilic coating may be applied to the covering material to improve the wettability and echo translucency of the covering material. In some embodiments, the covering material may be modified with chemical moieties that promote or inhibit one or more of endothelial cell attachment, endothelial cell migration, endothelial cell proliferation, and resistance to thrombosis. In some embodiments, the covering material may be modified with covalently attached heparin or impregnated with one or more drug substances that are released in situ.

In some embodiments, one or more cuff portions 220 are included on the exterior of structural framework 210, such as, but not limited to, at the proximal end in the depicted embodiment. Such cuff portions 220 may enhance sealing between prosthetic tricuspid valve 200 and the native anatomy, and may also enhance migration resistance in some circumstances. Cuff portion 220 may comprise a natural or a synthetic flexible sheet-like material. In some embodiments, cuff portion 220, or portions thereof, comprise a fluoropolymer, such as PTFE or an ePTFE polymer. In some embodiments, cuff portion 220, or portions thereof, comprises a polyester, a silicone, a urethane, other biocompatible polymers, DACRON®, copolymers, or combinations and subcombinations thereof. In some embodiments, cuff portion 220 can include natural tissues such as, but not limited to, bovine, porcine, ovine, or equine pericardium. In some such embodiments, the tissues are chemically treated using glutaraldehyde or formaldehyde or triglycidylamine (TGA) solutions or other tissue crosslinking agents.

In some embodiments, prosthetic tricuspid valve 200 includes multiple anchor features 230. Anchor features 230 comprise small protrusions that extend outward from the outer surface of structural framework 210. In some embodiments, the length of anchor features 230 are in a range from about 0.2 mm to about 0.5 mm, or from about 0.4 mm to about 0.8 mm, or from about 0.6 mm to about 1.0 mm, or about 0.9 mm to about 1.3 mm, or about 1.2 mm to about 1.6 mm, or about 1.5 mm to about 2.0 mm, or longer than about 2.0 mm.

In some embodiments, anchor features 230 extend outward from the outer surface of structural framework 210 at an angle such that anchor features 230 extend partially distally. For example, in some embodiments one or more of the anchor features 230 extend outward from the outer surface of structural framework 210 at an angle in a range from about 80° to about 90°, or from about 70° to about 80°, or from about 60° to about 70°, or from about 50° to about 90°, or from about 50° to about 60°, or from about 40° to about 50°, or from about 30° to about 40°, or from about 20° to about 30°, or from an angle that is less than about 20°.

In some embodiments, anchor features 230 are configured as hooks, barbs, spikes, eyelets, and the like, and are intended to penetrate tissue. In some embodiments, one or more of anchor features 230 are fixedly attached to structural framework 210. In particular embodiments, one or more of anchor features 230 are fixedly attached to other members, such as, but not limited to, the commissural posts of tri-leaflet valve assembly 240.

In some embodiments, anchor features 230 are comprised of a material such as nitinol, stainless steel, titanium, and the like, and combinations thereof.

Prosthetic tricuspid valve 200 also includes tri-leaflet valve assembly 240. In some embodiments, such as the depicted embodiment, tri-leaflet valve assembly 240 includes three leaflets 242a, 242b, and 242c that perform the occluding function of prosthetic tricuspid valve 200. Leaflets 242a, 242b, and 242c are fixed to three commissural posts 244a, 244b, and 244c. Commissural posts 244a, 244b, and 244c are disposed at about 120° apart from each other. In some embodiments, commissural posts 244a, 244b, and 244c each have a series of holes that can be used for attachment of leaflets 242a, 242b, and 242c, such as by suturing. The free edges of the three leaflets 242a, 242b, and 242c can seal by coaptation with each other during systole and open during diastole.

In some embodiments, leaflets 242a, 242b, and 242c are configured for substantial leaflet redundancy. That is, in some embodiments leaflets 242a, 242b, and 242c have lengths that allow for adequate coaptation over a broad range of diameters of prosthetic tricuspid valve 200. Such a feature is advantageous because, for example, the right ventricle and tricuspid annulus can tend to vary depending on the patient's volume status and loading conditions.

Leaflets 242a, 242b, and 242c can be comprised of natural or synthetic materials. For example, leaflets 242a, 242b, and 242c can be comprised of any of the materials described above in reference to cuff 220, including the natural tissues such as, but not limited to, bovine, porcine, ovine, or equine pericardium. In some such embodiments, the tissues are chemically crosslinked using glutaraldehyde or formaldehyde or triglycidylamine solution, or other suitable crosslinking agents. In some embodiments, leaflets 242a, 242b, and 242c have a thickness in a range of about 0.005" to about 0.020" (about 0.13 mm to about 0.51 mm), or about 0.008" to about 0.012" (about 0.20 mm to about 0.31 mm). In some embodiments, the leaflets 242a, 242b, and 242c have a thickness that is less than about 0.005" (about 0.13 mm) or greater than about 0.020" (about 0.51 mm).

In some embodiments, the occluding function of prosthetic tricuspid valve 200 can be performed using configurations other than a tri-leaflet occluder. For example, bi-leaflet, quad-leaflet, or mechanical valve constructs can be used in some embodiments.

In some embodiments, prosthetic tricuspid valve 200 includes a control string 250. Control string 250 is slidably attached to structural framework 210 such that tensioning control string 250 contracts structural framework 210, and slackening control string 250 allows for radial expansion of structural framework 210 (e.g., like a purse-string or lasso). In some embodiments, control string 250 is a suture, or a nitinol wire, and/or the like. Control string 250 can be tensioned or slackened by the clinician(s) that are performing the procedure to implant prosthetic tricuspid valve 200. Control string 250 also facilitates repositioning and/or retrieval of prosthetic tricuspid valve 200.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A prosthetic tricuspid valve comprising:
a structural framework of one or more braided nitinol wires arranged in a frustoconical shape that extends from a proximal end of the structural framework to a distal end of the structural framework, wherein the structural framework flares outward in a distal direction such that the proximal end of the structural framework is smaller than the distal end of the structural framework, the structural framework arranged to define an outer surface and an inner open region;
a cuff disposed on a proximal end portion of the outer surface, the cuff comprising a flexible covering material;
a plurality of anchor features, the anchor features extending outward from the outer surface, the anchor features configured for piercing tissue; and
a valve assembly disposed within the inner open region, the valve assembly comprising three leaflets that are configured for coaptation with each other,
wherein the prosthetic tricuspid valve is reconfigurable between a low-profile delivery configuration for containment within a delivery catheter and an expanded deployed configuration.

2. The prosthetic tricuspid valve of claim 1, wherein the structural framework has a linear outer wall profile between the proximal and distal ends of the structural framework.

3. The prosthetic tricuspid valve of claim 2, wherein the structural framework defines a non-circular transverse cross-sectional shape.

4. The prosthetic tricuspid valve of claim 1, wherein the flexible covering material comprises ePTFE or PTFE.

5. The prosthetic tricuspid valve of claim 1, wherein at least some of the anchor features extend outward from the outer surface at angles in a range from about 50° to about 90°.

6. The prosthetic tricuspid valve of claim 1, wherein at least some of the anchor features extend outward from the outer surface for distances in a range of about 0.6 mm to about 1.0 mm.

7. The prosthetic tricuspid valve of claim 1, wherein the structural framework self-expands from the low-profile delivery configuration to the expanded deployed configuration upon emergence from a delivery catheter.

8. A prosthetic tricuspid valve and deployment system comprising:
a delivery catheter that defines a lumen therein, the delivery catheter configured for percutaneous use;
a prosthetic tricuspid valve, wherein the prosthetic tricuspid valve is reconfigurable between a low-profile delivery configuration for containment within the lumen and an expanded deployed configuration, wherein the prosthetic tricuspid valve comprises:
a structural framework of one or more braided nitinol wires arranged in a frustoconical shape that extends from a proximal end of the structural framework to a distal end of the structural framework, wherein the structural framework flares outward in a distal direction such that the proximal end of the structural framework is smaller than the distal end of the structural framework, the structural framework arranged to define an outer surface and an inner open region;
a cuff disposed on a proximal end portion of the outer surface, the cuff comprising a flexible covering material;
a plurality of anchor features, the anchor features extending outward from the outer surface, the anchor features configured for piercing tissue; and
a valve assembly disposed within the inner open region, the valve assembly comprising three leaflets that are configured for coaptation with each other; and
a control string, the control string being slidably engaged with the structural framework such that tensioning the control string can cause the structural framework to contract and slackening the control string can allow the structural framework to expand.

9. The prosthetic tricuspid valve and deployment system of claim 8, wherein a distal end portion of the delivery catheter is selectively deflectable.

10. The prosthetic tricuspid valve and deployment system of claim 8, wherein the structural framework has a linear outer wall profile between the proximal and distal ends of the structural framework.

11. The prosthetic tricuspid valve and deployment system of claim 10, wherein the structural framework defines a non-circular transverse cross-sectional shape.

12. The prosthetic tricuspid valve and deployment system of claim 8, wherein the flexible covering material comprises ePTFE or PTFE.

13. The prosthetic tricuspid valve and deployment system of claim 8, wherein at least some of the anchor features extend outward from the outer surface at angles in a range from about 50° to about 90°.

14. The prosthetic tricuspid valve and deployment system of claim 8, wherein at least some of the anchor features extend outward from the outer surface for distances in a range of about 0.6 mm to about 1.0 mm.

15. The prosthetic tricuspid valve and deployment system of claim 8, wherein the structural framework self-expands from the low-profile delivery configuration to the expanded deployed configuration upon emergence from a delivery catheter.

16. A method of implanting a prosthetic tricuspid valve in a patient, the method comprising:
percutaneously installing a delivery catheter in the patient, wherein the delivery catheter defines a lumen therein, wherein the prosthetic tricuspid valve is disposed within the lumen in a low-profile delivery configuration, wherein the prosthetic tricuspid valve comprises:
a structural framework of one or more braided nitinol wires arranged in a frustoconical shape that extends from a proximal end of the structural framework to a distal end of the structural framework, wherein the structural framework flares outward in a distal direction such that the proximal end of the structural framework is smaller than the distal end of the structural framework, the structural framework arranged to define an outer surface and an inner open region;

a cuff disposed on a proximal end portion of the outer surface, the cuff comprising a flexible covering material;

a plurality of anchor features, the anchor features extending outward from the outer surface, the anchor features configured for piercing tissue; and a valve assembly disposed within the inner open region, the valve assembly comprising three leaflets that are configured for coaptation with each other;

navigating the delivery catheter within the patient such that a distal end of the delivery catheter is position adjacent a native tricuspid valve of the patient; and causing the prosthetic tricuspid valve to emerge from the lumen and to expand within the native tricuspid valve, wherein a majority of the prosthetic tricuspid valve is disposed below an annulus of the native tricuspid valve and within a right ventricle of the patient.

17. The method of claim 16, wherein the causing the prosthetic tricuspid valve to emerge from the lumen and to expand within the native tricuspid valve also causes at least some of the anchor features to penetrate one or more native leaflets of the native tricuspid valve.

18. The method of claim 17, wherein the prosthetic tricuspid valve further comprises a control string, the control string being slidably engaged with the structural framework such that tensioning the control string can cause the structural framework to contract and slackening the control string can allow the structural framework to expand.

19. The method of claim 18, further comprising, after causing the prosthetic tricuspid valve to emerge from the lumen and to expand within the native tricuspid valve, tensioning the control string to contract the structural framework such that the at least some of the anchor features that penetrated the one or more native leaflets are no longer penetrating the one or more native leaflets, and repositioning the prosthetic tricuspid valve within the native tricuspid valve.

* * * * *